Jan. 13, 1959 C. N. HASTIE, JR Plant Pat. 1,800
CAMELLIA PLANT
Filed June 9, 1958
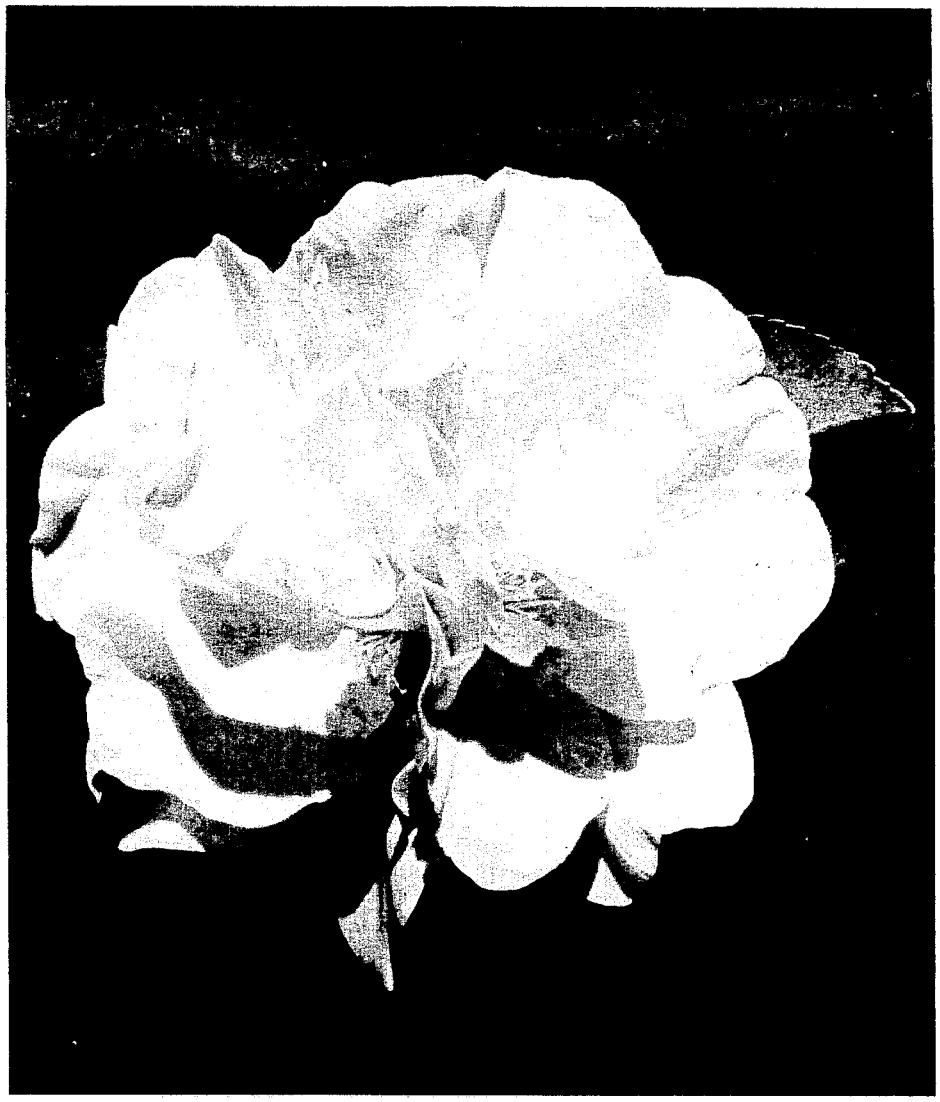
INVENTOR
C. N. Hastie, Jr.
BY Robb & Robb
ATTORNEYS United States Patent Office Plant Pat. 1,800
Patented Jan. 13, 1959

1,800

CAMELLIA PLANT

Carlisle Norwood Hastie, Jr., John's Island, S. C.

Application June 9, 1958, Serial No. 740,984

1 Claim. (Cl. 47—60)

The present invention relates to a new and distinct variety of camellia plant which was originated by me as a selected seedling of unknown parentage.

For many years, I have been growing camellia plants on my property near Charleston, South Carolina, and customarily have gathered seed from the plants, planted the seeds in special beds, and grown the seedlings therefrom for the purpose of seeking new and improved varieties. The present seedling is one of those which I planted in a bed with some 1800 other seedlings of various parentage, and because this particular seedling showed that it possessed unique and desirable characteristics when it first bloomed, it was carefully preserved and observed over a period of several years, and was ultimately asexually reproduced by me by both grafting and own-rooting of cuttings, as performed by me on my property near Charleston, South Carolina. Continued observations of the propagated plants have conclusively established that the variety has not varied from the parent plant, and that its characteristics are established and transmissible through succeeding propagations.

Among the outstanding features which contribute to the novelty and distinctiveness of my new variety are the following:

(1) Very vigorous and compact habits of growth;
(2) Ease of propagation;
(3) Good winter hardiness;
(4) Good plant shape;
(5) Good foliage of medium size and abundant quantity;
(6) Freedom from Glomerella disease;
(7) Heavy blooming habit;
(8) Good bloom form; and
(9) A distinctive and attractive Light Pink general color tonality of the blooms similar to that of "Debutante" (unpatented), but with a blooming period beginning just after that of "Debutante" finishes.

As yet, the new variety has shown no undesirable characteristics, which can be said of very few camellias, and it is definitely distinguished from all other varieties of which I am aware.

The accompanying drawing shows a typical specimen flower and some of the foliage of my new variety as depicted in color as nearly true as it is reasonably possible to make the same in a color illustration of this character.

The following is a detailed description of my new camellia, with color terminology in accordance with general color terms of ordinary dictionary significance, except where reference is made to Maerz and Paul Dictionary of Color, as indicated:

Parentage: Unknown.
Type: Japonica.

Propagation: Holds its distinguishing characteristics through succeeding propagations by both grafting and own-rooting.

Blooming habit: Midseason—from about mid-January to about the end of February.

Bud:
- *Size.*—Medium.
- *Form.*—Globular.
- *Sepals.*—Smooth edge.
- *Calyx.*—Broad.

Bloom:
- *Size (when fully open).*—From 4 inches to 5¼ inches.
- *Borne.*—Singly on strong stems.
- *Form.*—Loose semi-peony, both when first and fully open.
- *Petalage.*—Double; arranged irregularly.
- *Color.*—Light Pink, Plate 41 (Maerz and Paul), shading from tone F1 when first open, to a darker tone J1 as the flower ages.

Petals:
- *Texture.*—Soft.
- *Shape.*—Rounded.
- *Arrangement.*—Irregular; informal.

Genital organs:
- *Stamens, anthers.*—Medium size. Color—yellow. Arrangement—interspersed.
- *Stamens, filaments.*—Medium length. Color—white.
- *Styles.*—Columnar; medium length. Color—white.
- *Ovaries.*—All enclosed in calyx.
- *Fruit.*—None observed.

Plant:
- *Form.*—Compact.
- *Growth.*—Very vigorous.
- *Foliage.*—Size—medium; about 9 cm. long and 3.5 cm. wide. Quantity—abundant. Shape—oval; more rounded than most camellia leaves; with sharply pointed tip; moderately keeled. Texture: upper side—smooth; under side—smooth. Ribs and veins—ordinary. Edge—serrated. Color: new foliage—light green; old foliage—medium green.

Wood:
- *New wood.*—Color—light green, without any red coloring as is typical of some camellias.
- *Old wood.*—Color—brown, changing to gray as wood ages.

Disease resistance: Free of Glomerella disease, as determined by comparison with other varieties grown under comparable cultural conditions in the geographical area of Charleston, South Carolina.

I claim:

A new and distinct variety of camellia plant of the japonica type, substantially as herein shown and described, characterized particularly as to novelty by the unique combination of its very vigorous and compact habits of growth, ease of propagation, good winter hardiness, good plant shape, good foliage of medium size and abundant quantity, freedom from Glomerella disease, heavy blooming habit, good bloom form, and a distinctive and attractive Light Pink general color tonality of the blooms similar to that of the variety "Debutante" (unpatented), but with a blooming period beginning just after that of "Debutante" finishes.

No references cited.